United States Patent [19]

Wu

[11] Patent Number: 4,501,755
[45] Date of Patent: Feb. 26, 1985

[54] ISOFLAVONES USEFUL AS ANTI-INFLAMMATORY AGENTS

[75] Inventor: Edwin S. Wu, Rochester, N.Y.

[73] Assignee: Pennwalt Corporation, Philadelphia, Pa.

[21] Appl. No.: 441,889

[22] Filed: Nov. 15, 1982

Related U.S. Application Data

[63] Continuation-in-part of Ser. No. 259,403, May 1, 1981, abandoned, and a continuation-in-part of Ser. No. 422,929, Sep. 24, 1982, abandoned.

[51] Int. Cl.³ .................... A61K 31/35; C07D 311/36
[52] U.S. Cl. .................................... 514/456; 549/403
[58] Field of Search ................ 549/401, 403; 424/283

[56] References Cited

U.S. PATENT DOCUMENTS 4,391,821  7/1983  Korbonits et al. .................. 424/283

OTHER PUBLICATIONS

Korbonits et al., Chem. Abstr., 97, 198,113h (1982)–Abstract of Brit. UK Pat. Appl. GB 2,089,338 (6-23-82).

Primary Examiner—Nicky Chan

[57] ABSTRACT

Chromone derivatives such as 7-(3-amino-2-hydroxypropoxy)-3-phenylchromones which are useful for preparing other chemical compounds and for pharmaceutical uses such as antihypertensive and anti-inflammatory agents.

10 Claims, No Drawings

ISOFLAVONES USEFUL AS ANTI-INFLAMMATORY AGENTS

This is a continuation-in-part of U.S. Ser. No. 259,403 filed May 1, 1981 and U.S. Ser. No. 422,929 filed Sept. 24, 1982, both now abandoned.

BACKGROUND OF THE INVENTION

This invention relates to chromone derivatives substituted by 3-amino-2-hydroxypropoxy side chains, which are useful as antihypertensive or anti-inflammatory agents in animals.

U.S. Pat. No. 3,891,651 discloses compounds which are amides and, it is thought, the nitrogen of the amide which is contained in the isoquinoline fragment is likely to be responsible for any activity in that compound. U.S. Pat. No. 3,816,470 discloses various salts of secondary amines with chromone-2-carboxylic acids. U.S. Pat. No. 3,812,156 discloses a method of preparing ethyl flavone-7-oxyacetate. U.S. Pat. No. 3,352,754 discloses simple 7-hydroxy or 7-alkoxy isoflavones which are not amines and which are used for various inflammatory disorders. U.S. Pat. No. 3,219,531 discloses 5,7-dioxyacetic acid flavone compounds, but no amine functions are present. U.S. Pat. No. 3,046,275 discloses 7-dialkylaminoalkoxy derivatives but does not contain any of the hydroxyl groups of the side chain. Various monodialkyl aminoethyl ethers of quercetin are disclosed in U.S. Pat. No. 2,861,992, but do not contain 3-amino-2-hydroxypropoxy side chains. Also not containing that side chain are the compounds disclosed in U.S. Pat. No. 2,897,211. P. Da Re et al., *J. Med. Chem.*, Vol. 15, 868–869 (1972), discloses related chromones and typical 3-amino-2-hydroxypropoxy side chain furochromone compounds are disclosed in papers presented in *Drugs of the Future*, Vol. III, No. 8 (1978), pages 569–571; *Drugs of the Future*, Vol. III, No. 11, (1978), pages 816–818; and *Therapie*, (1977), Vol. 32, pages 111–120. Wang et al., *Acta Pharmaceutica Sinica*, Vol. 15, pages 253–256 (1980) also discloses structurally related compounds. None of the references is considered to teach the invention of the present application.

SUMMARY OF THE INVENTION

The present invention provides a compound of the formula

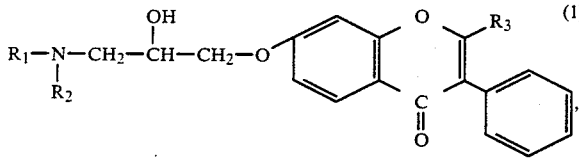

or a pharmaceutically acceptable acid addition or quaternary ammonium salt thereof and where $R_1$ and $R_2$ are hydrogen, lower alkyl or cycloalkyl and $R_3$ is hydrogen, lower alkyl, $CF_3$, cycloalkyl or heterocyclic such as furyl.

The compounds are usually mixed with a pharmaceutical carrier so that the composition for commercial use contains 0.5 to 20% by weight of the compound.

The compositions are normally adapted for peroral or parenteral use, but may be used in other forms such as suppositories. The peroral compositions are preferably in the form of tablets, capsules or suspensions, while the parenteral composition is preferably an injectable solution or suspension.

Examples of suitable inert pharmaceutical carriers are celluloses (particularly microcrystalline celluloses), sugar syrups, potato starch, talcum, polyethylene glycols and lactose.

Examples of suitable acids for forming the acid addition salts are maleic acid, hydrochloric acid, sulfuric acid, phosphoric acid, methanesulfonic acid, tartaric acid, citric acid, and the cation exchange resins such as the carboxylic acid, phosphonic acid and sulfonic acid resins.

For sustained release, a coated complex of the compound absorbed onto an ion exchange resin may be employed in accordance with the teaching of British Pat. No. 1,544,761.

The usual peroral dosage of the compound is 0.1 to 150 mg. per day (preferably 0.1 to 50 mg.) while the parenteral dosage is normally 0.1 to 40 mg. per day (preferably 0.1 to 10 mg.).

The capsules, tablets, syrups and suspensions of the compounds are prepared by conventional procedures.

DESCRIPTION OF THE INVENTION

The compounds of formula (1) above can be prepared by reacting epichlorohydrin or epibromohydrin with a compound of the formula

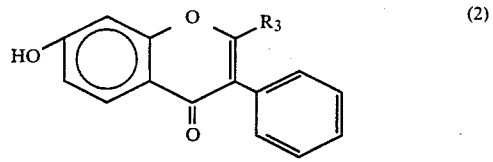

wherein $R_3$ is the same as defined above in the presence of a solvent and a base to give a product of formula (2) where the hydrogen of the hydroxyl group has been substituted by

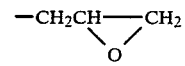

This epoxide is allowed to react with ammonia or an amine, of the formula $R_4NH_2$ or $R_4R_5NH$ where $R_4$ and $R_5$ are lower alkyl, cycloalkyl or benzyl, in an alcoholic solvent at elevated temperature to afford a product of formula (1). When $R_5$ is benzyl, it can be removed by catalytic hydrogenation to give the secondary amine.

The following general procedures are used in the examples to follow:

A. For Epoxides

Epichlorohydrin or epibromohydrin (greater than 2 equivalents) is added in the presence or absence of nitrogen to a stirred solution or suspension of the hydroxy chromone derivative in solvents, such as acetone, aqueous ethanol, 50% aqueous dimethylsulfoxide (DMSO) or water, containing a suitable base, such as potassium carbonate or sodium hydroxide, with or without sodium iodide. The reaction is allowed to proceed either at room temperature or elevated temperature and monitored by thin layer chromatography (tlc). The product, formed as solid, is then collected and washed with water. The mother liquor is diluted with water and extracted with chloroform ($CHCl_3$) to give more product. Where the product is soluble in solvents, the reaction mixture is filtered off and the solids washed with the solvent. The filtrate is evaporated to give a solid which is washed with water to get rid of remaining traces of the base. Yield is in the 60 to 80% range. This material is usually used directly for further reaction without purification.

B. For Epoxide Ring-Opening With Amine and the Amine Salt Formation

A white suspension of the chromone epoxide, ammonia or amine, such as low (large excess) and high (10% excess) boiling point amines, and alcoholic solvent, methanol (A.R.) ethanol (abs.) or isopropanol, is heated at elevated temperatures until the starting material is gone (as followed by tlc.) Since the reaction product is usually soluble in the alcohol, the precipitate is filtered off and the filtrate is evaporated to give a viscous liquid which, upon addition of anhydrous ether or alcohol, crystallizes out. When the product is insoluble in alcohol at the end of the reaction, it is collected. Purification of the amine derivative is performed via acid-base work-up, column chromatography or recrystallization. The amine obtained is either suspended or dissolved in an alcohol, such as MeOH or abs. ethanol (EtOH) or isopropanol, and then acidified with alcoholic solution saturated with hydrogen chloride or another suitable acid. The salt formed is precipitated out by addition of anhydrous either. The salt is then recrystallized from suitable solvents.

EXAMPLE 1

Preparation of
7-(2-hydroxy-3-isopropylaminopropoxy)-3-phenylchromone hydrochloride 7-(2,3-Epoxypropoxy)-3-phenylchromone 7-Hydroxy-3-phenylchromone and epichlorohydrin were reacted according to general procedure A, and the product obtained was white prisms, m.p. 151°–152° (83% crude yield) from isopropyl alcohol.

7-(2-Hydroxy-3-isopropylaminopropoxy)-3-phenylchromone hydrochloride 7-(2,3-Epoxypropoxy)-3-phenylchromone and isopropylamine were reacted according to Method B to give the product as the hydrochloride in 62% yield, mp. 148°–150° (EtAC-EtOH-Ether). Its corresponding free base, m.p. 128°–130°.

Anal. Calc'd. for $C_{21}H_{24}ClNO_4$: C, 64.69; Cl, 9.09, H, 6.20; N, 3.59. Found: C, 64.63; H, 6.30; Cl, 9.65; N, 3.56.

EXAMPLE 2

Preparation of
7-(2-hydroxy-3-isopropylaminopropoxy)-2-methylisoflavone hydrochloride 7-(2,3-epoxypropoxy)-2-methylisoflavone Using Method A, the epoxide was synthesized from 7-hydro-2-methylisoflavone as white prisms.

7-(2-hydroxy-3-isopropylaminopropoxy)-2-methylisoflavone hydrochloride

The title compound was prepared as described in Method B from the above epoxide and isopropylamine as white prisms; m.p. 183°–5° (iPrOH), in 40% yield.

Anal. Calc'd. for $C_{22}H_{26}ClNO_4$: C, 65.42; H, 6.49; N, 3.47; Cl, 8.78. Found: C, 65.25; H, 6.74; N, 3.39; Cl, 8.67.

EXAMPLE 3

Preparation of
7-(3-N-methyl-N-isopropylamino-2-hydroxypropoxy)-2-methylisoflavone methiodide 7-(2-hydroxy-3-isopropylaminopropoxy)-2-methylisoflavone (8.1 g, 0.021 moles) was added to a small amount of dry ether. The ethereal solution under nitrogen was allowed to react with methyl iodide (9.0 ml) and stirred overnight. The solid formed was collected and washed with anhydrous ether. It was recrystallized twice from ethanol (abs.) to give 6.8 g (62% yield) of light yellow powder; m.p. 211°–213° C.

Anal. Calc'd. for $C_{24}H_{30}NO_4I$: C, 55.07; H, 5.77, I, 24.24; N, 2.67. Found: C, 54.89; H, 5.80; I, 24.06; N, 2.49

EXAMPLE 4

Preparation of
7-(2-hydroxy-3-isopropylaminopropoxy)-2-trifluoromethylisoflavone hydrochloride 7-(2,3-epoxypropoxy)-2-trifluoromethylisoflavone The epoxide was prepared from 7-hydroxy-2-trifluoromethylisoflavone following Method A: m.p. 146°–148° ($CH_2Cl_2$); yield, 61%.

7-(2-hydroxy-3-isopropylaminopropoxy)-2-trifluoromethylisoflavone hydrochloride

Reaction of the corresponding epoxide with isopropylamine, as shown in Method B, afforded the title compound as white prisms, m.p. 220°–222° C.

Anal. Calc'd. for $C_{22}H_{23}ClFNO_4$: C, 57.71; H, 5.06; Cl, 7.74; F, 12.44; N, 3.05. Found: C, 57.88; H, 5.06; Cl, 7.52; F, 12.51; N, 2.97.

EXAMPLE 5

Preparation of
7-(2-hydroxy-3-isopropylaminopropoxy)-2-isopropylisoflavone maleate 7-(2,3-epoxypropoxy)-2-isopropylisoflavone The epoxide was prepared from 7-hydroxy-2-isopropylisoflavone by Method A; m.p. 139°–140° C. ($CH_2Cl_2$); yield, 27%.

7-(2-hydroxy-3-isopropylaminopropoxy)-2-isopropylisoflavone maleate

The corresponding epoxide was reacted with isopropylamine followed by maleic acid to give the maleate as white prisms in 94% yield, m.p. 187°–188°.

Anal. Calc'd. for $C_{28}H_{33}NO_8$: C, 65.74; H, 6.50; N, 2.73. Found: C, 65.77; H, 6.27;, N, 2.66.

EXAMPLE 6

Preparation of
7-(2-hydroxy-3-propylaminopropoxy)-2-trifluoromethylisoflavone hydrochloride Reaction of the corresponding epoxide with propylamine (Method B) afforded the salt as white prisms, m.p. 169°–171° (iPrOH—MeOH).

Anal. Calc'd for $C_{22}H_{23}NO_4ClF_3$; C, 57.71; H, 5.06; N, 3.05; Cl, 7.74, F, 12.44. Found: C, 57.63; H, 5.11; N, 3.02; Cl, 7.52; F, 12.34.

EXAMPLE 7

Preparation of 7-(2-hydroxy-3-isopropylaminopropoxy)-2-cyclohexylisoflavone hydrochloride 7-(2,3-epoxypropoxy)-2-cyclohexylisoflavone The epoxide was prepared from 7-hydroxy-2-cyclohexylisoflavone following Method A; m.p. 163°–165°; yield, 87%.

7-(2-hydroxy-3-isopropylaminopropoxy)-2-cyclohexylisoflavone hydrochloride

The crude epoxide was reacted with isopropylamine, using Method B, to give the hydrochloride salt as white prisms, m.p. 217°–219° (MeOH—iPrOH).

Anal. Calc'd for $C_{27}G_{34}NO_4Cl$: C, 68.68; H, 7.52; Cl, 7.51; N, 2.97; O, 13.56. Found: C, 68.34; H, 7.31; Cl, 7.79; N, 2.93; O, 13.63.

EXAMPLE 8

Preparation of 7-(2-hydroxy-3-cyclooctylaminopropoxy)-isoflavone hydrochloride

Using Method B, the reaction of 7-(2,3-epoxypropoxy)isoflavone with cyclooctylamine followed by acidification of the resulted free base with HCl/EtOH gave the hydrochloride as light yellow prisms, m.p. 185°–186° (iPrOH).

Anal. Calc'd for $C_{26}H_{32}NO_4Cl$; C, 68.19; H, 7.04; Cl, 7.74; N, 3.06. Found: C, 68.55; H, 6.99; Cl, 7.75; N, 3.13.

EXAMPLE 9

Preparation of 7-(2-hydroxy-3-N-methyl-N-isopropylaminopropoxy)-2-methylisoflavone hydrochloride The title compound was prepared according to Method B; m.p. 169°–171° (iPrOH—Ether).

Anal. Calc'd for $C_{23}H_{28}NO_4Cl$: C, 66.10; H, 6.75; N, 3.35; Cl, 8.48. Found: C, 66.40; H, 6.84; N, 3.32; Cl, 8.61.

Anti-inflammatory Activity

These properties were determined by carrageenan-induced paw edemas of test rats. Male, Sprague-Dawley rats (Blue Spruce Farm) were ordered at 124–140 g, housed for one week, and allowed food and water ad libitum. At the time of the experiments, only rats weighing 160–200 g were used.

All compounds were dissolved or suspended in a 0.5% water solution of Methocel and orally administered to groups of six rats each. Control rats received Methocel only. Two hours later, paw edema was induced by subcutaneous injection into the plantar surface of the right hind paw of 0.1 ml of a 1.0% homogenized suspension of carrageenan.

Immediately, the volume of the paw was measured by immersing it in mercury to above the lateral mateolus. The mercury in a glass cylinder 22 mm in diameter and 60 mm deep was connected at the bottom of the cylinder by a column of water to a Statham transducer (model P23BB), range 0–5 cm of mercury pressure. The volume was recorded electronically on a Beckman recorder, R511. Three hours later, the inflamed paw volume was measured again, and the change in volume was recorded for each group. The percent inhibition of edema was calculated using the control group paw volume as 100% edema, i.e., $$\frac{\text{Control group edema } \Delta - \text{test group edema } \Delta}{\text{control group edema}} \times 100 =$$

| Ex. No. | Dose (mg/kg p.o.) | % Inhibition of Edema % Inhibition |
|---------|-------------------|-----------------------------------|
| 1 | 50 | 45 |
| 4 | 50 | 31 |
| 5 | 50 | 29 |

Many equivalent modifications will be apparent to those skilled in the art from a reading of the above without a departure from the inventive concept.

What is claimed is:

1. A compound of the formula

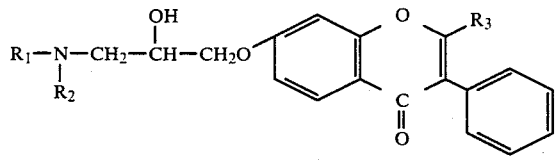

or a pharmaceutically acceptable acid addition or quaternary ammonium salt thereof and where $R_1$ is hydrogen, lower alkyl or cycloalkyl of up to six carbon atoms, $R_2$ is hydrogen or methyl and $R_3$ is hydrogen, lower alkyl, $CF_3$, cycloalkyl or furyl.

2. The compound 7-(2-hydroxy-3-isopropylaminopropoxy)-3-phenylchromone hydrochloride.

3. The compound 7-(2-hydroxy-3-isopropylaminopropoxy)-2-methylisoflavone hydrochloride.

4. The compound 7-(3-N-methyl-N-isopropylamino-2-hydroxypropoxy)-2-methylisoflavone methiodide.

5. The compound 7-(2-hydroxy-3-isopropylaminopropoxy)-2-trifluoromethylisoflavone hydrochloride.

6. The compound 7-(2-hydroxy-3-isopropylaminopropoxy)-2-isopropylisoflavone maleate.

7. The compound 7-(2-hydroxy-3-propylaminopropoxy)-2-trifluoromethylisoflavone hydrochloride.

8. The compound 7-(2-hydroxy-3-isopropylaminopropoxy)-2-cyclohexylisoflavone hydrochloride.

9. The compound 7-(2-hydroxy-3-N-methyl-N-isopropylaminopropoxy)-2-methylisoflavone hydrochloride.

10. A process for treating a warm-blooded animal for inflammation in need of such treatment which comprises administering to such animal an effective amount of the compound of claim 1.

* * * * *